United States Patent
Geiger (10) Patent No.: US 11,382,703 B2
(45) Date of Patent: Jul. 12, 2022

(54) SURGICAL ASSISTANCE SYSTEM AND METHOD FOR GENERATING CONTROL SIGNALS FOR VOICE CONTROL OF A SURGICAL ASSISTANCE SYSTEM ROBOT KINEMATICS THAT CAN BE MOVED IN A MOTOR-CONTROLLED MANNER

(71) Applicant: Aktormed GmbH, Barbing (DE)

(72) Inventor: Robert Geiger, Metten (DE)

(73) Assignee: Aktormed GmbH, Barbing (DE)

( * ) Notice: Subject to any disclaimer, the term of this patent is extended or adjusted under 35 U.S.C. 154(b) by 359 days.

(21) Appl. No.: 16/478,294

(22) PCT Filed: Jan. 29, 2018

(86) PCT No.: PCT/EP2018/052113
§ 371 (c)(1),
(2) Date: Jul. 16, 2019

(87) PCT Pub. No.: WO2018/138325
PCT Pub. Date: Aug. 2, 2018

(65) Prior Publication Data
US 2019/0365488 A1    Dec. 5, 2019

(30) Foreign Application Priority Data
Jan. 30, 2017    (DE) .......................... 102017101782.8

(51) Int. Cl.
*G06F 19/00*   (2018.01)
*A61B 34/30*   (2016.01)
(Continued)

(52) U.S. Cl.
CPC .............. *A61B 34/30* (2016.02); *A61B 34/35* (2016.02); *B25J 9/1694* (2013.01); *B25J 13/003* (2013.01);
(Continued)

(58) Field of Classification Search
CPC ... A61B 34/30; A61B 34/35; A61B 2034/302; A61B 2034/742; A61B 2017/00203; A61B 2017/00212; B25J 9/1694; B25J 13/003
See application file for complete search history.

(56) References Cited

U.S. PATENT DOCUMENTS

| 6,591,239 B1 * | 7/2003 | McCall | G10L 15/26 704/275 |
| 2005/0033580 A1 * | 2/2005 | Wang | A61B 1/0016 704/275 |

(Continued)

FOREIGN PATENT DOCUMENTS

| WO | 9609587 A1 | 3/1996 |
| WO | 2013186794 A2 | 12/2013 |

OTHER PUBLICATIONS

International Preliminary Report on Patentability, PCT Division, dated Jul. 30, 2019.

*Primary Examiner* — Harry Y Oh
*Assistant Examiner* — Sohana Tanju Khayer
(74) *Attorney, Agent, or Firm* — Welsh Flaxman & Gitler LLC (57) ABSTRACT

The invention relates to an operation-assistance system for guiding a medical auxiliary instrument (20), which can be inserted in an operating site (12) of a patient body (10) via an operation opening (11), and can be moved in a controlled manner. The system comprises a kinematic robot (3, 4, 5) that receives the medical auxiliary instrument (20) on the free end thereof by means of an auxiliary instrument holding device (6), and can be moved in a motor-controlled manner in order to guide the medical auxiliary instrument (20) in the operating site (12), by means of control signals (SS) generated by a control unit (CU). At least one voice control routine (SSR) is implemented in the control unit (CU), by (Continued)

means of which different voice commands (SB, SB1, SB2) are detected and evaluated and associated control signals (SS) are determined in accordance.

5 Claims, 4 Drawing Sheets

(51) Int. Cl.
  *B25J 9/16* (2006.01)
  *B25J 13/00* (2006.01)
  *A61B 34/35* (2016.01)
  *A61B 34/00* (2016.01)
  *A61B 17/00* (2006.01)

(52) U.S. Cl.
  CPC ............... *A61B 2017/00203* (2013.01); *A61B 2017/00212* (2013.01); *A61B 2034/302* (2016.02); *A61B 2034/742* (2016.02)

(56) References Cited

U.S. PATENT DOCUMENTS

| | | | |
|---|---|---|---|
| 2013/0096575 A1* | 4/2013 | Olson | A61B 34/76 606/130 |
| 2013/0297319 A1* | 11/2013 | Kim | G10L 15/22 704/275 |
| 2015/0088060 A1* | 3/2015 | Wang | A61M 25/0105 604/95.03 |
| 2017/0133011 A1* | 5/2017 | Chen | G10L 25/78 |

* cited by examiner

SURGICAL ASSISTANCE SYSTEM AND METHOD FOR GENERATING CONTROL SIGNALS FOR VOICE CONTROL OF A SURGICAL ASSISTANCE SYSTEM ROBOT KINEMATICS THAT CAN BE MOVED IN A MOTOR-CONTROLLED MANNER

BACKGROUND OF THE INVENTION

1. Field of the Invention

The invention relates to a surgery assistance system and a method for generating control signals for voice control of a motor-controlled movable robot kinematics of a surgery assistance system.

2. Description of the Related Art

Surgery assistance systems, in particular for supporting medical procedures or operations, in particular minimally invasive operations, are generally known.

Such surgery assistance systems are frequently used for the guidance of medical auxiliary instruments, e.g. camera systems, in particular so-called endoscope cameras. Document DE 10 2007 019363 A1 for example discloses a surgery assistance system, by means of which for example an endoscope comprising a camera unit or an endoscope camera, respectively, is guided in a controlled manner. To this end the surgery assistance system comprises a robot kinematics drivable in a controlled manner, by means of which an endoscope camera received on an instrument holder is movable in a controlled manner in a three-dimensional space, in particular in the operating space. The robot kinematics for example comprise at least two robot arms and at least an instrument carrier receiving the instrument holder.

Further, DE 10 2008 016 146 B4 discloses a method for guiding a medical auxiliary instrument, in particular an endoscope camera, by means of such a surgery assistance system, specifically dependent on manual actuation of at least one function key of an operating element. The medical auxiliary instrument is attached to an arm system of the surgery assistance system with an instrument holder, and the tip of the surgical auxiliary instrument is movable by means of the arm system in a Cartesian patient coordinate system in a controlled manner, wherein at least one of the three spatial axes of the Cartesian patient coordinate system extends through the surgical opening receiving the medical auxiliary instrument or through the Trocar point. Disadvantageously, in order to control guidance of the medical auxiliary instrument, in particular an endoscope camera, an operating part connected to a computer system is required, for example in the form of a foot switch, joy stick or manual operating element, which has to be actuated by the surgeon in addition to a medical operating instrument, with which he performs the surgical procedure. This requires that the surgeon, in order to achieve correct guidance of the medical auxiliary instrument in the operating space, has to manually actuate the corresponding function keys of the operating part, in particular in accordance with the image of the operating space displayed on a monitoring unit.

Furthermore, voice-operated control systems for such surgery assistance systems are already known, where the surgeon, via voice commands, can control the guidance of the auxiliary instrument via the robot kinematics. The disadvantage is that the range of functions of such voice control systems is limited and, therefore, the task of approaching a target position in a precise manner is not very user-friendly.

SUMMARY OF THE INVENTION

Starting from this it is an object of the invention to provide a surgery assistance system, in particular also for medical interventions or operations, as well as an associated method for generating control signals for voice control of the robot kinematics of such a surgery assistance system. The present invention allows the surgeon to achieve a more precise and user-friendly voice control of guiding the medical auxiliary instrument via the surgery assistance system, when performing a surgical procedure.

This object is met by a surgery assistance system for guiding a medical auxiliary instrument, in particular an endoscope camera, which can be inserted via a first surgical opening into an operating space of a patient body, at least in sections, and which is movable in a controlled manner. Robot kinematics receive the medical auxiliary instrument by means of an auxiliary instrument holder on the free end side, wherein the robot kinematics can be moved in a motor-controlled manner via control signals generated by a control unit for guiding the medical auxiliary instrument in the operating space. At least one voice control routine is executed in the control unit, via which different voice commands are detected and evaluated and control signals ascertained in dependence thereof are determined. The voice control routine is configured for detecting and evaluating voice command combinations consisting of at least a first and a second voice command, wherein direction or speed information is assigned to the first voice command and amount information is assigned to the second voice command in a reference coordinate system. Depending on the detected direction or speed information and the detected amount information of the voice command combination at least one associated control signal is ascertained, via which at least the movement of the medical auxiliary instrument is controlled with respect to direction or speed and amount. The direction information indicates the direction of movement of the auxiliary instrument in the Cartesian reference coordinate system and the amount information indicates the path length or route along the direction of movement in the Cartesian reference coordinate system.

Further the requirement is met by a method for generating control signals for controlling a motor-controlled movable robot kinematics of a surgery assistance system for guiding a medical auxiliary instrument, in particular an endoscope camera, in which the medical auxiliary instrument is arranged via an auxiliary instrument holder on the free end side on the robot kinematics. The medical auxiliary instrument can be inserted via a first surgical opening into the operating space of a patient body, at least in sections, and in which the control signals are determined by means of at least one voice control routine executed in a control unit. By means of the voice control routine a voice command combination consisting of at least a first and second voice command is detected and evaluated, wherein direction or speed information is assigned to the first voice command and amount information is assigned to the second voice command in a reference coordinate system. Depending on the detected direction or speed information and the detected amount information of the voice command combination at least one associated control signal is determined, via which at least the movement of the medical auxiliary instrument is controlled with respect to direction and amount. The direction information indicates the direction of movement of the auxiliary instrument in the Cartesian reference coordinate system and the amount information indicates the path length or route along the direction of movement in the Cartesian reference coordinate system.

An essential aspect of the surgery assistance system according to the invention is that the voice control routine is configured to record and evaluate voice command combinations consisting of at least a first and a second voice command, wherein direction or speed information is assigned to the first voice command and amount information is assigned to the second voice command in a reference coordinate system. The first and second voice commands directly following one another in terms of time are recorded and evaluated by the voice control routine within a pre-set time duration. Depending on the recorded direction and speed information and the recorded amount information of the voice command combination at least one associated control signal is ascertained, via which at least the movement of the medical auxiliary instrument is controlled as regards direction or speed and amount. The direction information indicates the direction of movement of the auxiliary instrument in the Cartesian reference coordinate system and the amount information indicates the path length or route along the movement direction in the Cartesian reference coordinate system. Particularly advantageously, the surgeon, via inputting a voice command combination, can simultaneously set the direction of movement or the speed and the associated amount and thereby control the movement of the auxiliary instrument much more precisely, wherein especially advantageously the direction information indicates the direction of movement of the auxiliary instrument in the Cartesian reference coordinate system and the amount information indicates the path length or route along the direction of movement in the Cartesian reference coordinate system. Thus, more complex control tasks can be realised by means of simple voice commands, since the surgeon is able, due to the inventive combination of simple voice commands, to himself create a more complex control command specific to the application without having to learn further control commands.

Further, the voice control routine is advantageously configured to detect and evaluate first and second voice commands directly one after the other within a pre-set duration of time. If the pre-set time interval is exceeded, a sequence of two successive voice commands is not recognized as a voice command combination, but as individual voice commands, respectively, which are to be detected and evaluated independently of one another.

Further advantageously the first and second voice commands comprise one or more words. This makes it possible to use intuitively descriptive words and word combinations for voice control.

In a preferred embodiment, voice control by means of the voice control routine is active only when the surgeon actuates an activating element, preferably an activating switch or button, or if an activating voice command is present.

Furthermore, the actual position of the auxiliary instrument can be advantageously stored by means of a third voice command with respect to the reference coordinate system and again selectively retrieved by means of a fourth voice command at a later point in time.

The terms "approximately", "essentially" or "roughly" in terms of the invention are understood to mean deviations by +/−10%, preferably by +/−5% from the respectively exact value and/or deviations in the form of changes insignificant for the function.

Further developments, advantages and possible applications of the invention are also revealed in the description hereunder of exemplary embodiments and the figures. All described and/or figuratively depicted features are in principle a subject of the invention either on their own or in any random combination, independently of their summary in the claims or reference thereto. Also, the content of the claims is made part of the description.

BRIEF DESCRIPTION OF THE DRAWINGS

The invention will now be discussed in detail by way of the figures using exemplary embodiments, in which.

DESCRIPTION OF THE PREFERRED EMBODIMENTS

Figure 1:
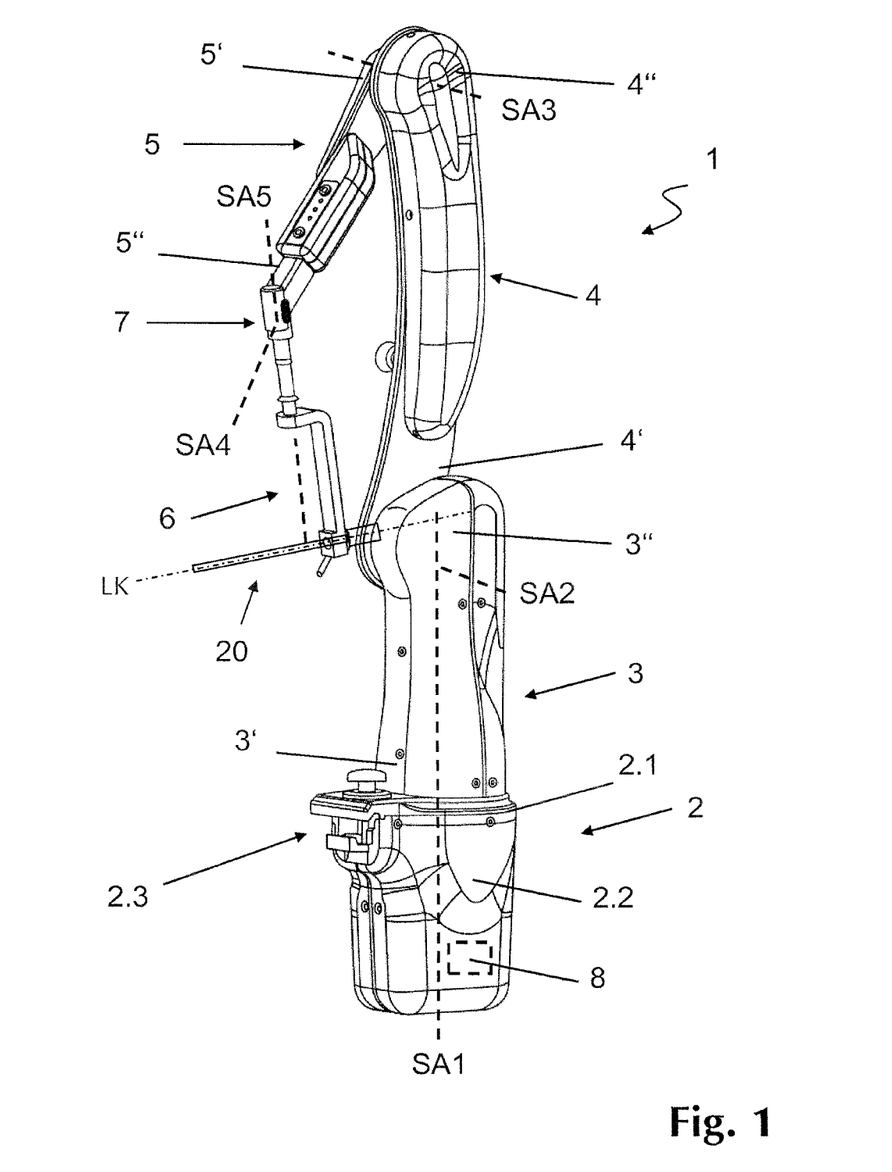
FIG. 1 shows a schematic side view of a surgery assistance system.

FIG. 1, by way of example, shows a surgery assistance system 1 for guiding medical auxiliary instruments 20 in medical interventions or operations in or on a patient body 10. A medical auxiliary instrument 20 in terms of the invention is understood to be, in particular, an endoscope camera, which essentially consists of an endoscope 21 and a camera unit 22 arranged at its free end.

Figure 2:
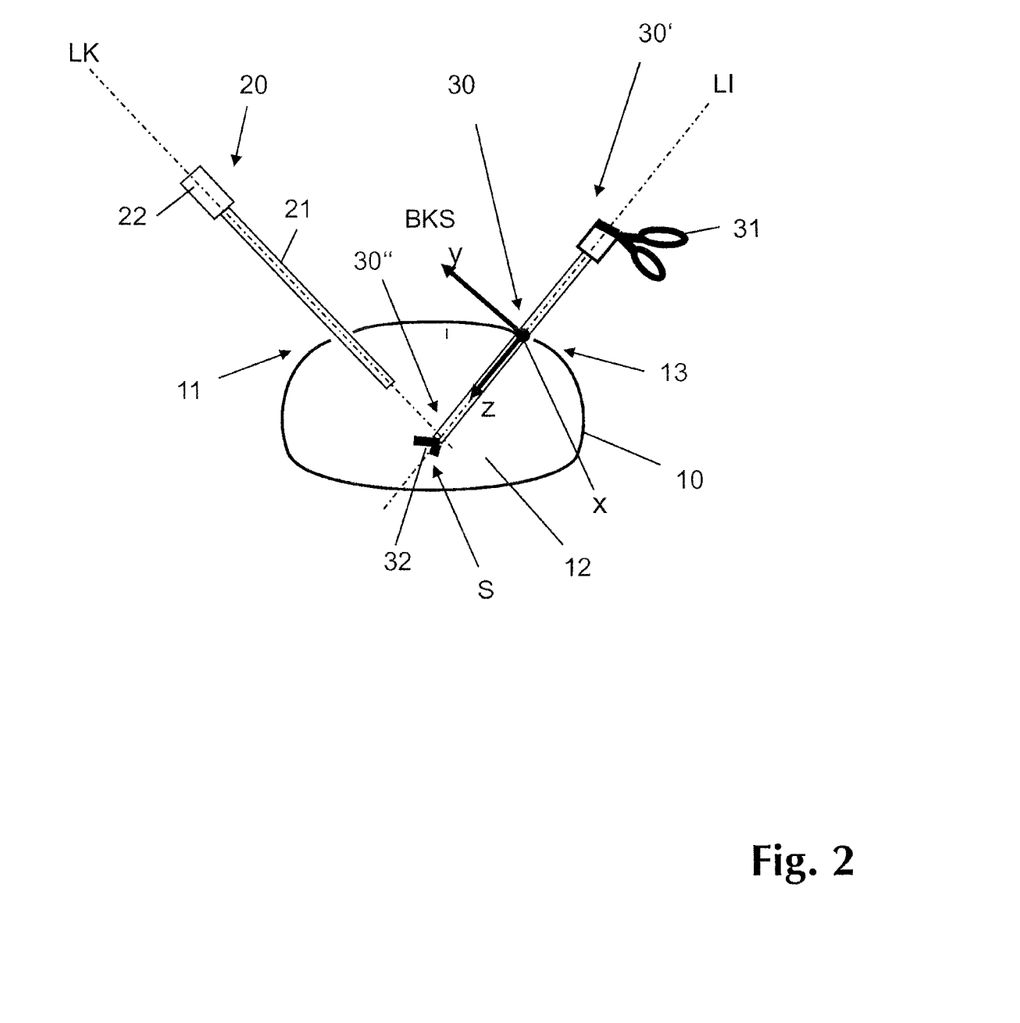
FIG. 2 shows a schematic sectional view through a patient body with an endoscope camera accommodated at least in sections in the operating space and a medical surgery instrument.

Such endoscope cameras 20 are frequently used in minimally invasive operations, and these are inserted via a small-format first surgical opening 11 into an operating space 12 within a patient body 10. The medical or operating instrument 30, as such for performing the medical procedure, is inserted via a second surgical opening 13 into the operating space 12 of the patient body 10. In the literature the first and second surgical openings 11, 13 are frequently denoted with "Trocar" or "Trocar points". FIG. 2 schematically depicts a typical operating situation by way of example as a section through a patient body 10 in the minimally invasive operating region.

Using the endoscope camera 20, or its camera unit 22, photos or pictures of the operating space 12, including of the tip S of the medical instrument 30 in the operating space, are taken. The pictures are displayed to the surgeon during the medical procedure or the minimally invasive operation by means of a monitor unit. By means of the current pictures ("live pictures") of the operating space 12 displayed on the monitor unit the surgeon can monitor the course of the operation and guide the medical instrument or operating instrument 30, accordingly. In order to always be able to see a current and optimal image of the operating space 12, in particular of the medical instrument or the operating instrument 30, it is of major importance to the surgeon to be able to optimally activate or operate, in particular also align and/or adjust, the endoscope camera 22.

The surgery assistance system 1 according to the invention makes it possible for the surgeon to operate and guide the auxiliary instrument, in particular the endoscope camera 20, in a highly precise and user-friendly manner by means of "voice control". To this end the surgery assistance system 1 consists for example of a base unit 2 and a robot kinematics comprising a system of several arms, in particular robot arms. The robot kinematics, in the present example, comprises a support column 3, first and second robot arms 4, 5 and an auxiliary instrument carrier 6. The auxiliary instrument carrier 6 is for example hinged on the second robot arm 5, here by means of an angled-off hinge piece 7. The auxiliary instrument carrier 6 is for example configured for directly receiving the medical auxiliary instrument, that is the endoscope camera 20, or for indirectly receiving the latter via a further auxiliary instrument holder not shown in the figures. The described construction of the robot kinematics of the surgery assistance system 1 is revealed by way of example in the perspective view of the surgery assistance system 1 of FIG. 1.

The base unit 2 further comprises for example a carrier plate 2.1, a preferably multi-part base housing 2.2 and at least one fastening element 2.3, by means of which the preferably portably configured surgery assistance system 1 or the base unit 2 can be fastened laterally on an operating table (not shown in the figures). The base housing 2.2 houses at least a control device 8 and, as required, further functional units, which cooperate, as required, with a computer system not shown.

The support column 3 comprises an upper and a lower end portion 3', 3". The base unit 2 of the surgery assistance system 1 is connected to the lower end portion 3' of the support column 3 of the robot kinematics so as to be pivoted about a first pivot axis SA1 in a controlled manner. The first pivot axis SA1 extends perpendicularly to the installation plane of the surgery assistance system 1 or the operating plane or plane of an operating table, respectively.

The first robot arm 4 further comprises first and a second end portions 4', 4", wherein the first end portion 4' of the first robot arm 4 is connected to the upper end portion 3" of the support column 3 opposite the base unit 2 so as to be pivoted about a second pivot axis SA2 in a controlled manner. The second end portion 4" of the first robot arm 4 is connected to a first end portion 5' of the second robot arm 5 so as to be pivoted about a third pivot axis SA3 in a controlled manner.

The second robot arm 5 comprises a second end portion 5" opposite the first end portion 5', on which in the present exemplary embodiment the angled-off hinge piece 7 is provided so as to be rotatable about a fourth pivot axis SA4. The angled-off hinge piece 7 is configured to receive a connecting portion of the auxiliary instrument carrier 6, in such a way as to be rotatable about a fifth pivot axis SA5 and so as to be detachable. The opposite free end of the auxiliary instrument carrier 6 forms an instrument holder.

The first pivot axis SA1 extends perpendicularly to the installation plane or operating plane and the second and third pivot axes SA2, SA3 run parallel to each other, whereas the first pivot axis SA1 is orientated vertically to the second or third pivot axis SA2, SA3.

A number of drive units not shown in the figures are provided for driving the robot kinematics of the surgery assistance system 1, and these are configured so as to be controlled via a control device 8, preferably independently of one another. The drive units are preferably integrated or received in the base unit 2, the support column 3 and/or in the robot arms 4 to 6. The drive units may, for example, be formed as hydraulic drives or electrical drives, in particular linear motor units or spindle motor units.

The at least one control device 8 is preferably received in the base unit 2 of the surgery assistance system 1 and serves to generate control signals for activating the drives or drive units for pivoting the robot kinematics in a controlled motoric manner about the defined pivot axes SA1 to SA5 and/or for holding the robot kinematics in a defined holding position in a Cartesian coordinate system.

The support column 3 extends vertically, i.e. essentially along the first pivot axis SA1, i.e. it is designed so as to be rotatable about approximately its own longitudinal axis. The first and second robot arms 4, 5 essentially also extend along a straight, which preferably extends vertically to the second or third pivot axis SA2, SA3. In the present exemplary embodiment at least the first robot arm 4 is lightly curved.

In order to set the starting position of the surgery assistance system 1 or to calibrate the control device 8 with regard to the first surgical opening 11 or Trocar point, through which the medical auxiliary instrument 20 is inserted into the operating space, a registration routine is provided, by means of which prior to the operation the surgery assistance system 1 is registered. For example, a registering feeler not shown in the figures is guided to that region of the patient already on the operating table, in which the first surgical opening 11 for inserting the medical auxiliary instrument 20 is provided. Following this calibration the surgery assistance system 1 is then ready to guide the medical auxiliary instrument, in particular the endoscope camera 20.

FIG. 2 shows a schematic side view of an endoscope camera 20 inserted via the first surgical opening 11 into the operating space 12 of the patient body 10. Furthermore FIG. 2 shows a medical instrument or surgical instrument 30 inserted into the operating space 12 via the second surgical opening 13. The second surgical opening 12 here forms for example the origin of a reference coordinate system BKS with the spatial axes x, y, z.

In FIG. 2 the x-axis of the Cartesian reference coordinate system BKS extends for example vertically to the drawing plane, the y-axis of the Cartesian reference coordinate system BKS extends vertically to the longitudinal axis LI of the medical instrument 30, and the z-axis extends along the longitudinal axis LI of the medical instrument 30 or coincides with the same. The origin is to be found in the region of the second surgical opening 12. With such an orientation of the Cartesian reference coordinate system BKS a rotation about the longitudinal axis LI of the medical instrument 30 advantageously corresponds to a respective rotation about the z-axis, which allows a simplified evaluation of a rotational movement about the longitudinal axis LI of the medical instrument 30.

The medical instrument or the operating instrument 30 comprises for example at its free end 30' at least one, preferably two grip elements 31, which are formed for example as two grip rings with respectively adjoining connecting shaft. A function element 32, for example a gripping or cutting element arranged at the opposite free end 30" of the medical instrument or operating element 30 can be actuated via at least one of the grip elements 31. The function element 32 forms the tip S of the medical instrument 30, which during the procedure is in the operating space 12 and is being recorded by the endoscope camera 20. The free end 30' is outside the patient body 10 and is the gripping region of the medical instrument or operating instrument 30.

A control unit CU, by means of which control signals SS are generated with respect preferably to the Cartesian reference coordinate system, is provided for controlling the movement of the auxiliary element 20 within the operating space 12. These signals are transmitted to the control device

Figure 3:
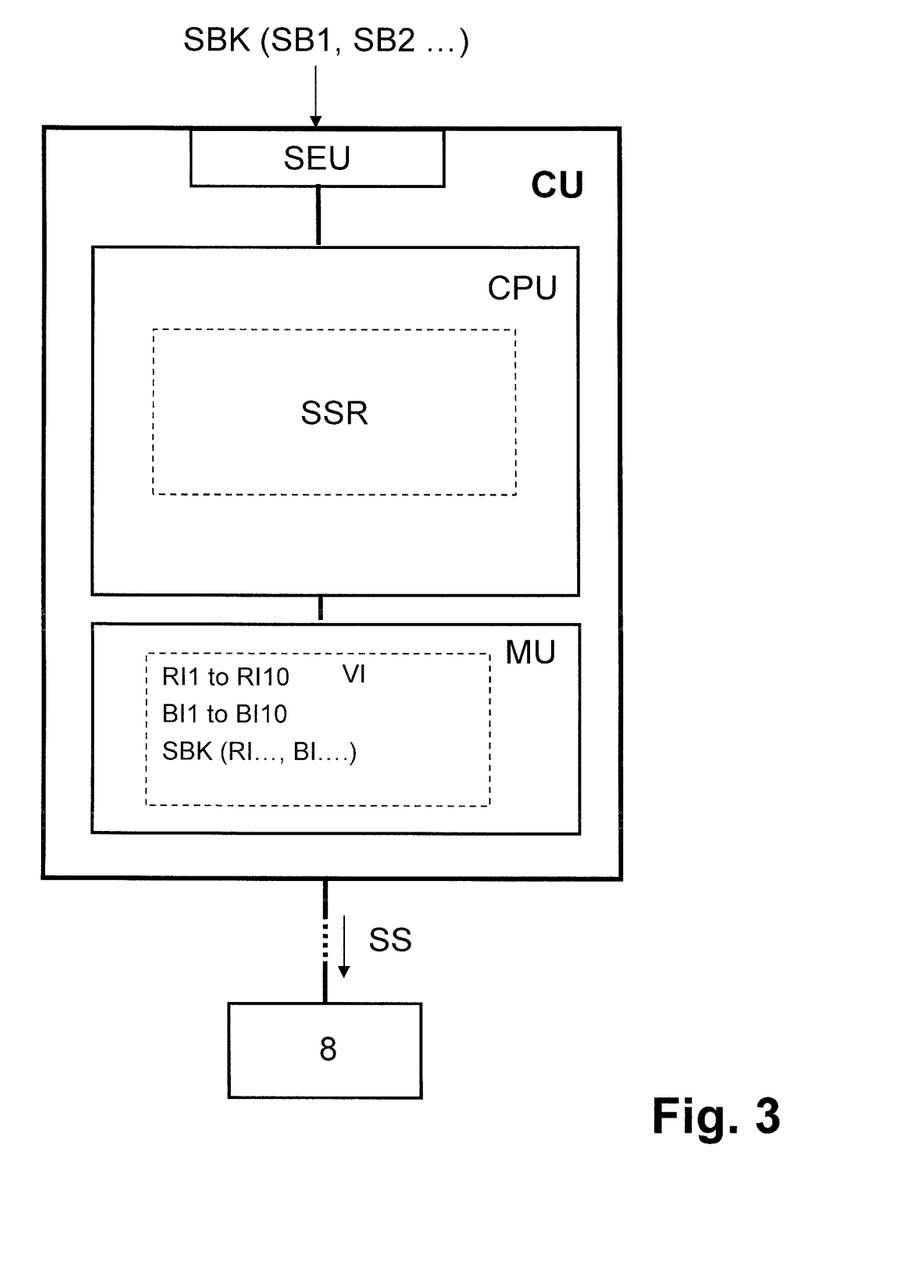
FIG. 3 shows a schematic block diagram of a sensor unit according to the invention for detecting the movement data of the medical operating instrument, and FIGS. 4a, b show schematic top views of a diagram in the x-y-plane or x-z plane, respectively, of a Cartesian reference coordinate system comprising various movement and amount information.

8, by means of which the drives or drive units of the robot kinematics are respectively controlled for pivoting the support column 3 and/or the robot arms 4, 5 of the robot kinematics in a motor-controlled manner, in order to initiate a rotational and/or pivoting movement about the defined pivot axes SA1 to SA5 and/or a stop of the robot kinematics in a defined holding position with respect to the reference coordinate system BKS.

According to the invention, the control unit CU comprises at least a voice control routine SSR, which is used to generate control signals SS via voice commands SB, SB1, SB2 of the surgeon during the operation.

Such a "voice control" of the robot kinematics, and thus of the movement of the auxiliary element 20 in the operating space 12, allows the surgeon, with the aid of respective defined voice commands SB, SB1, SB2, to cause the auxiliary element, in particular the endoscope camera 20, to track the medical instrument 30 and/or to change the image of the operating space 12 generated by the camera unit 22 according to the current requirements through a corresponding movement of the endoscope camera 20. The use of voice controls for an at least partial control of operating robots is known, wherein known systems only have a limited range of functions and relatively low control accuracy.

This is where the invention starts and allows the surgeon to exercise a more precise and also user-friendly voice control. According to the invention, the voice control routine SSR is configured for detecting and evaluating voice command combinations SBK consisting of at least a first and a second voice command SB1, SB2, wherein at least direction information RI or speed information VI is assigned to the first voice command SB1 and at least amount information BI is assigned to the second voice command SB2, each with respect to the Cartesian reference coordinate system BKS. It is understood that a combination of voice commands SBK can of course comprise more than two voice commands SB1, SB2 etc., so that for example apart from direction or speed information and amount information RI, BI, further movement information in the form of further voice commands SB can be passed to the voice control routine SSR. In the present exemplary embodiment, however, the invention is explained in more detail by way of a voice command combination SBK comprising two voice commands SB1, SB2. The invention is however by no means limited thereto.

The control unit CU comprises at least a processing unit CPU and a voice signal detecting unit SEU and for example a storage unit MU. The voice signal detecting unit SEU is configured for detecting the control command SB, SB1, SB2 spoken by the surgeon in the form of for example voice signals comprising one or more words. The voice signal accordingly detected via the voice signal detecting unit SEU forms the control command SB, SB1, SB2, which is transmitted to the voice control routine SSB executed in the processor unit CPU. In the storage unit MU of the control unit CU, each inventive voice command combination SBK, which can be generated from the available control commands SB1, SB2, may be assigned a control signal SS, which causes a respective control of the robot kinematics by means of the control device 8. Alternatively a suitable control signal SS can be ascertained based on the detected and evaluated control commands SB1, SB2.

In addition to the voice control according to the invention a manually actuated input unit may be provided, for example in form of a remote control, a joystick or other input unit comprising a number of switching elements, via which the required control signals SS can be generated additionally or alternatively to the voice control routine SSR. The surgeon can then choose between different input units.

According to the invention, the voice commands generated by the surgeon, i.e. the first and second voice commands SB1, SB2 directly following one another chronologically, are detected and evaluated within a pre-set time duration. Depending on the direction and speed information R1, VI and the further amount information BI of a voice command combination SBK detected via the voice commands SB1, SB2, at least one control signal SS is generated or ascertained, via which at least the movement of the medical auxiliary instrument 20 is controlled with regard to direction and amount.

A first or second voice command SB1, SB2 as understood by the invention may comprise one or more words or word components, which are spoken either on their own or in combination directly following one another and to each of which direction information RI or speed information VI or amount information BI are assigned in the voice control routine SSR.

For the purpose of control first voice commands SB1 with a defined number of different direction information RI or different speed information and second voice commands SB2 with a defined number of different amount information BI are available to the surgeon. The start point is always a current existing actual position of the auxiliary instrument 20 in the reference coordinate system BKS in order to reach a defined required position in the reference coordinate system BKS.

Direction information RI in terms of the invention is understood to mean a defined movement direction of the auxiliary instrument 20 in the reference coordinate system BKS from an actual position to a required position, which is preferably defined in the form of a direction vector which is oriented from the actual position to the required position.

Amount information BI in terms of the invention is understood to mean the amount of movement of the auxiliary instrument 20 along the direction of movement in the reference coordinate system BKS, as defined by the direction information RI or the direction vector, respectively, wherein the amount essentially specifies the path length or route to be travelled during the movement, starting from the actual position of the auxiliary instrument 20 in order to reach the desired required position. An even more accurate approach to the required position in the reference coordinate system BKS as desired is possible via the inventive combination of direction information RI and amount information BI in a voice command combination SBK, which moreover is extremely user-friendly for the surgeon.

Speed information VI in terms of the invention is understood to mean one or more defined speeds which indicate the speed of movement, with which the auxiliary instrument 20 is moved via the robot kinematics in the Cartesian reference coordinate system.

Figure 4A:
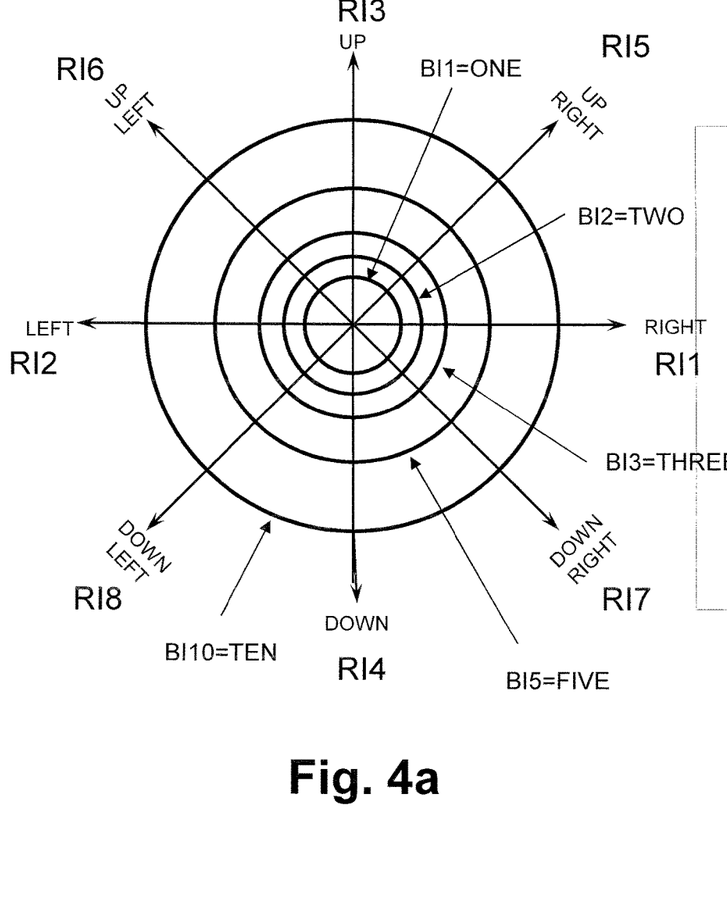
Figure 4B:
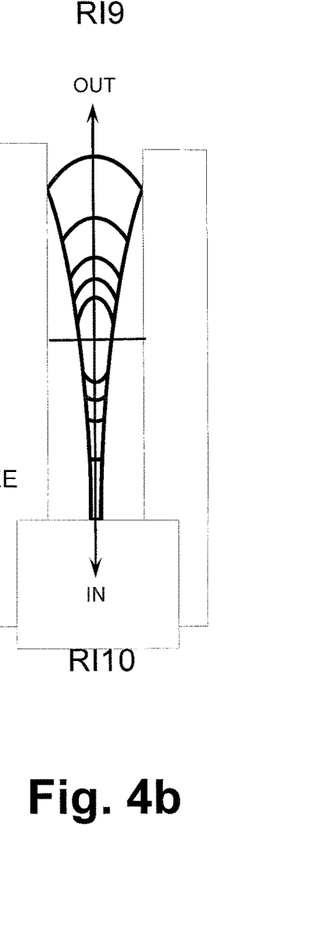

FIGS. 4a and 4b show, by way of example, different direction information RI1-RI10 and amount information BI1-BI10, which may be the subject of the first or second voice command SB1, SB2.

FIG. 4a, by way of example, shows a top view of the x-y-plane of the reference coordinate system BKS and FIG. 4b shows a top view of x-z-plane of the reference coordinate system BKS with the different direction and amount information RI, BI depicted therein as an example.

FIG. 4a, for example, shows a first voice command SB1 with the wording "RIGHT", to which first direction information RI1 is assigned, which coincides with the x-axis and points in the positive x-direction. Further, a first voice command SB1 with the wording "LEFT" is provided, to which second direction information RI2 is assigned. The second direction information RI2 in turn corresponds to the x-axis direction, but in the negative x-direction. Analogously thereto provision is made for a first voice command SB1 with the wording "UP" with third direction information RI3 and an alternative first voice command SB1 with the wording "DOWN" with fourth direction information RI4. The third and fourth direction information RI3 correspond to the y-axis direction, i.e. in positive y-direction on the one hand, and in negative y-direction on the other. Finally, as an example, the following are offered as first voice commands SB1: the wording "UP RIGHT" referring to fifth direction information RI5, the wording "UP LEFT" referring to sixth direction information RI6, the wording "DOWN RIGHT" referring to seventh direction information RI7, and the wording "DOWN LEFT" referring to eighth direction information RI8, in the x-y-plane. The fifth direction information RI5, starting from the centre of the reference coordinate system BKS as angle bisector of the respectively positive x- and y-axis, points in positive x- and y-direction. The sixth direction information RI6, starting from the centre of the reference coordinate system BKS as angle bisector of the negative x-axis and the positive y-axis, points in negative x-direction and positive y-direction. The seventh direction information RI7, starting from the centre of the reference coordinate system BKS as angle bisector of the positive x-axis and negative y-axis, points in positive x-direction and negative y-direction. The eighth direction information R18, starting from the centre of the reference coordinate system BKS as angle bisector of the respectively negative x- and y-axis, points in negative x- and y-direction. The fifth to eighth direction information R15 to R18 thus indicate diagonally extending movement directions in the x-y-plane of the reference coordinate system BKS.

Finally FIG. 4b depicts, by way of example, two further options of a first voice command SB1, i.e. ninth direction information R19 assigned to the wording "OUT", which starting from the centre of the reference coordinate system BKS, coincides with the z-axis and extends in negative z-direction, and tenth direction information RI10 assigned to the wording "IN", which starting from the centre of the reference coordinate system BKS also coincides with the z-axis, but extends in positive z-direction. Therefore, in the present exemplary embodiment, 10 different movement information RI1 to RI10 is available to the surgeon for controlling the movement of the auxiliary instrument 20 or the endoscope camera, each comprising one or two words.

Further, according to the invention a voice command combination SBK additionally also comprises amount information BI1 to BI10 which can be individually combined with the respective direction information RI1 to RI10, wherein the amount information forms the second voice command SB2 and preferably follows the wording of the first voice command SB1. The present embodiment provides for first to tenth amount information BI1 to BI10, each indicating an amount or path length along the direction of movement defined by the respective direction information RI1 to RI10.

For example, a time interval may be assigned to the amount information BI1 to BI10, which indicates the time duration of the movement of the auxiliary instrument along the defined movement direction. Starting from a preferably constant movement speed, which again may be set via associated voice commands SB, this then leads to a route or path length travelled during this time interval. In a preferred variant depicted in the present embodiment the first to tenth amount information BI1 to BI10 respectively corresponds to a multiple of a predetermined reference path length or reference route, i.e. the first amount information BI1 corresponds to the one-times reference path length, the second amount information BI2 corresponds to a two-times path length, and so on. Accordingly, the second voice command SB2 may comprise a different wording. In the present embodiment for example, the wording "ONE" is assigned the first amount information BI1, the wording "TWO" is assigned the second amount information BI2, the wording "THREE" is assigned the third amount information BI3 etc. In FIG. 4a only the first to third, the fifth and the tenth amount information BI1 to BI3, BI5 and BI10 are shown, for example. The wording of the second voice command SB2 to be spoken by the surgeon thus corresponds to the respective number from 1 to 10 in the English language. The associated number respectively indicates the multiple of the reference path length assigned to the first amount information BI1.

In an alternative variant not explicitly shown in the figures, amount information BI1 to BI10 can of course be provided, which does not represent a multiple of a reference path length, but which is individually fixed. Preferably at least two amount information BI1 to BI10 with different amounts or path lengths or speeds can be combined with the above mentioned direction information RI1 to RI10.

Instead of a time interval an amount information BI1 to BI10 may also be assigned a concrete path length or route, which is chosen individually or can be set by the surgeon for personalising a system.

In an alternative variant not shown in the figures at least a speed information VI may be provided which has, as the first voice command SB1, the wording "SPEED" assigned to it and which is assigned a defined reference speed. The second voice command SB2 of the voice command combination SBK may comprise, analogously to the above described embodiment, different amount information BI1 to BI10, which respectively comprises a multiple of the reference speed.

In a preferred variant the voice control is activated via the voice control routine SSR only when the surgeon actuates an activation element, preferably an activation switch or button, or when he issues a defined activation voice command.

The current actual position of the auxiliary instrument 20 can also be stored in the Cartesian reference coordinate system via a voice control command SB in the storage unit MU of the control unit CU. By inputting a further voice command SB the stored actual position can again be selectively retrieved at a later point in time.

The invention has been described above with reference to exemplary embodiments. It is understood that numerous changes and modifications are possible without departing from the inventive idea underlying the invention.

REFERENCE LIST 1 surgery assistance system
2 base unit
2.1 carrier plate
2.2 base housing
2.3 fastening element
3 support column
3' lower end portion
3" upper end portion
4 first robot arm
4' first end portion
4" second end portion
5 second robot arm 5' first end portion
5" second end portion
6 auxiliary instrument carrier
7 angled-off hinge piece
8 control device
10 patient body
11 first surgical opening (Trocar)
12 operating space
13 second surgical opening (Trocar)
20 auxiliary instrument, in particular endoscope camera
21 endoscope
22 camera unit
30 medical instrument
30' free end/gripping region
30" free end
31 grip element
32 function element
BI amount information
BI1 to BI10 first to tenth amount information
BKS Cartesian reference coordinate system
CU control unit
LI longitudinal axis
LK longitudinal axis
RI direction information
RI1 to RI10 first to tenth direction information
S tip of the medical instrument
SA1 first pivot axis
SA2 second pivot axis
SA3 third pivot axis
SA4 fourth pivot axis
SA5 fifth pivot axis
SB control command
SB1 first control command
SB2 second control command
SBK control command combination
SS control signals
VI speed information
x, y, z spatial axes of Cartesian reference coordinate system

The invention claimed is:

1. A surgery assistance system for guiding a medical auxiliary instrument into an operating space of a patient body, at least in sections, and which is movable in a controlled manner, comprising:
robot kinematics receiving the medical auxiliary instrument by an auxiliary instrument holder on a free end side, wherein the robot kinematics can be moved in a motor-controlled manner via control signals generated by a control unit for guiding the medical auxiliary instrument in the operating space, wherein at least one voice control routine is executed in the control unit, via which different voice commands are detected and evaluated and control signals ascertained in dependence thereof are determined, the voice control routine is configured for detecting and evaluating voice command combinations including at least a first and a second voice command, wherein direction or speed information is assigned to the first voice command and amount information is assigned to the second voice command in a Cartesian reference coordinate system, and depending on the detected direction or speed information and the amount information of the voice command combinations at least one associated control signal is ascertained, via which at least movement of the medical auxiliary instrument is controlled with respect to direction or speed and amount of information, wherein the direction information indicates direction of movement of the medical auxiliary instrument in the Cartesian reference coordinate system and the amount information indicates a path length or route along the direction of movement in the Cartesian reference coordinate system, wherein the voice control routine is arranged for detecting and evaluating the first and the second voice commands directly chronologically following one another within a pre-set time interval, and if the pre-set time interval is exceeded, a sequence of two successive voice commands is not recognized as a voice command combination, but as individual voice commands and the individual voice commands are detected and evaluated independently of one another.

2. The surgery assistance system according to claim 1, wherein the first and second voice commands each comprise one or more words.

3. The surgery assistance system according to claim 1, wherein voice control is activated by the voice control routine only if the surgeon actuates an activation element or if an activation voice command is present.

4. The surgery assistance system according to claim 1, wherein the actual position of the medical auxiliary instrument with regard to the reference coordinate system can be stored by a third voice command and can be retrieved again in a targeted manner by a fourth voice command.

5. A method for generating control signals for controlling motor-controlled movable robot kinematics of a surgery assistance system for guiding a medical auxiliary instrument, in which the medical auxiliary instrument is arranged via an auxiliary instrument holder on a free end side on the robot kinematics, in which the medical auxiliary instrument can be inserted via a first surgical opening into an operating space of a patient body, at least in sections, and in which the control signals are determined by at least one voice control routine executed in a control unit, wherein by the voice control routine a voice command combination including at least a first voice command and a second voice command are detected and evaluated, comprising the steps of:
assigning a direction or speed information to the first voice command and assigning amount information to the second voice command in a Cartesian reference coordinate system, and depending on the direction or speed information and the amount information of the voice command combinations at least one associated control signal is determined, via which at least movement of the medical auxiliary instrument is controlled with respect to direction or speed and amount, wherein the direction information indicates a direction of movement of the auxiliary instrument in the Cartesian reference coordinate system and the amount of information indicates the path length or route along the direction of movement in the Cartesian reference coordinate system, wherein first and second voice commands directly chronologically following one another are detected and evaluated by the voice control routine within a pre-set time interval, and if the pre-set time interval is exceeded, a sequence of two successive voice commands is not recognized as a voice command combination but as individual voice commands and the individual voice commands are detected and evaluated independently of one another.

* * * * *